_US005834634A_

United States Patent [19]
Honda et al.

[11] Patent Number: 5,834,634
[45] Date of Patent: Nov. 10, 1998

[54] METHOD AND APPARATUS FOR MEASURING THE TONER CONCENTRATION AND THE AMOUNT OF ELECTRIC CHARGE OF A TWO-COMPONENT DEVELOPING AGENT

[75] Inventors: Koji Honda; Haruo Koyama; Yusuke Ishitani; Nobuaki Kawano, all of Osaka, Japan

[73] Assignee: Mita Industrial Co., Ltd., Osaka, Japan

[21] Appl. No.: 726,326

[22] Filed: Oct. 3, 1996

[30] Foreign Application Priority Data

Oct. 3, 1995 [JP] Japan ................................. 7-256572

[51] Int. Cl.⁶ ........................ G01N 15/06; G01N 27/00; G01N 27/74
[52] U.S. Cl. .................... 73/53.01; 73/61.71; 73/61.72; 73/64.56; 324/71.1; 324/204; 399/30; 399/62
[58] Field of Search ................... 73/83.01, 61.71, 73/61.72, 64.54, 64.56; 389/77, 30, 58, 62; 324/71.1, 204; 118/689

[56] References Cited

U.S. PATENT DOCUMENTS

| | | |
|---|---|---|
| 3,821,938 | 7/1974 | Bacon et al. ........................... 399/30 |
| 4,590,142 | 5/1986 | Yamazaki et al. ..................... 430/138 |
| 5,116,711 | 5/1992 | Kobayashi et al. ................... 430/106 |
| 5,470,687 | 11/1995 | Mayama et al. ..................... 430/137 |

*Primary Examiner*—Daniel S. Larkin
*Attorney, Agent, or Firm*—Sherman and Shalloway

[57] ABSTRACT

A method and an apparatus for measuring the toner concentration and the amount of electric charge, capable of simultaneously measuring the toner concentration and the amount of electric charge easily and maintaining high precision using a simple device. A method of measuring the toner concentration and the amount of electric charge of a two-component developing agent, by filling a unit cell having a mesh in the lower portion thereof and a small ventilation port at the upper central portion thereof with a two-component developing agent consisting of a toner and a magnetic carrier, creating a downward stream of the developing agent at the central portion of the unit cell and an upward stream of the developing agent along the walls of the unit cell relying upon the suction through said mesh, discharging the separated toner out of the unit cell through the mesh, calculating the toner concentration from the reduction in the weight of the developing agent in the unit cell or from the amount of the discharged toner and calculating the amount of electric charge from the amount of electric charge of the unit cell.

8 Claims, 3 Drawing Sheets

METHOD AND APPARATUS FOR MEASURING THE TONER CONCENTRATION AND THE AMOUNT OF ELECTRIC CHARGE OF A TWO-COMPONENT DEVELOPING AGENT

BACKGROUND OF THE INVENTION

1. Field of the Invention

The present invention relates to a method and an apparatus for measuring the toner concentration and the amount of electric charge of a two-component developing agent. More specifically, the invention relates to a method and an apparatus for simultaneously measuring the toner concentration and the amount of electric charge maintaining high precision using a simple device.

2. Prior Art

In the fields of electrophotographic copy and facsimile, there has been extensively used a two-component developing agent, i.e., a mixture of a magnetic carrier and an electroscopic toner in order to visualize electrostatic latent images.

In the magnetic brush developing method using a two-component developing agent, the developing agent is electrically charged upon the friction between the magnetic carrier and the electroscopic toner. The electrically charged developing agent rubs, in the form of a magnetic brush, the photosensitive material having electrostatic latent image, the toner is attracted by the electrostatic latent image, and the carrier remains on the developing roller equipped with a magnet, so that the developing operation is accomplished.

The toner concentration and the amount of electric charge of the two-component developing agent seriously affect the image density that is formed, image quality, and fogging. In the field of electrophotography, therefore, it is very important to measure the toner concentration and the amount of electric charge maintaining precision with simple operation.

So far, the amount of electric charge of the toner has been measured by a method in which the toner is separated from the developing agent using a gas pressure and the electric charge of the remaining carrier is measured (blow-off method 1-1), a method in which the migration of electric charge due to developing is measured as an electric current and the amount of electric charge of the toner particles is calculated (developing current method 1-2), a method in which the toner migration rate in the electric field is measured and the amount of electric charge of the toner particles is calculated (electric field migration method 1-3), and a method in which the surface potential of the developed toner is measured and the amount of electric charge of the toner particles is calculated (surface potential method 1-4).

Furthermore, the toner concentration is measured by a method in which the amount of carbon dioxide generated from the developing agent at high temperatures is measured and the amount of toner is calculated from the amount of carbon (carbon analyzer method 2-1) or a method in which the toner only in the developing agent is removed by washing and the toner concentration is calculated relying upon a difference in the weight (washing method 2-2).

According to the blow-off method 1-1 for measuring the amount of electric charge of the toner, however, the carrier is destroyed by the gas pressure and the electric charge that is generated at this moment is measured, too. Besides, the toner concentration must have been known, giving inconvenience. According to the developing current method 1-2, the electric current is so weak that the measurement is affected by noises and loses stability. According to the electric field migration method 1-3, it is difficult to separate the toner particles into individual particle and, besides, the apparatus becomes very complex and large in size. According to the surface potential method 1-4, it is difficult to accurately measure the thickness of the developed toner layer and the distance.

Even in measuring the toner concentration according to the above-mentioned carbon analyzer method 2-1, preliminary testing must be conducted concerning a developing agent of which the concentration has been known to formulate a conversion formula, spent toner adhered on the carrier surfaces is measured, too, the apparatus becomes very bulky, and very high costs are required for the articles of consumption and for the measurement. According to the washing method 2-2, great amounts of labor and time are required for the measurement offering poor measuring precision.

SUMMARY OF THE INVENTION

It is therefore an object of the present invention to provide a method and an apparatus for measuring the toner concentration and the amount of electric charge, capable of simultaneously measuring the toner concentration and the amount of electric charge easily and maintaining high precision using a simple device, without being accompanied by the above-mentioned defects inherent in the prior art.

According to the present invention, there is provided a method of measuring the toner concentration and the amount of electric charge of a two-component developing agent, by filling a unit cell having a mesh in the lower portion thereof and a small ventilation hole at the upper central portion thereof with the two-component developing agent consisting of a toner and a magnetic carrier, creating a downward stream of the developing agent at the central portion of the unit cell and an upward stream of the developing agent along the walls of the unit cell relying upon the suction through said mesh, discharging the separated toner out of the unit cell through the mesh, calculating the toner concentration from the reduction in the weight of the developing agent in the unit cell or from the amount of the discharged toner and calculating the amount of electric charge of the toner from the amount of electric charge of the unit cell.

According to the present invention, there is further provided an apparatus for measuring the toner concentration and the amount of electric charge of a two-component developing agent, comprising a unit cell for measurement having a two-component developing agent space therein, a mesh in the lower portion thereof and a single ventilation hole in the upper central portion thereof; a suction chamber; and a hollow unit cell support plate which is provided at an upper part of the suction chamber maintaining air-tightness and electric insulation and is also serving as an electrode; wherein the ventilation hole in said unit cell has an area which is from 1.6 to 25% of the mesh area, and the developing agent space in the unit cell has a height which is from 0.5 to 1.25 times as great as the diameter of the mesh.

In the apparatus of the present invention, it is desired that the unit cell and the support plate are made of metal materials having a difference in the work function which is not larger than 0.60 eV and, most desirably, the unit cell and the support plate are made of the same metal material.

Figure 3:
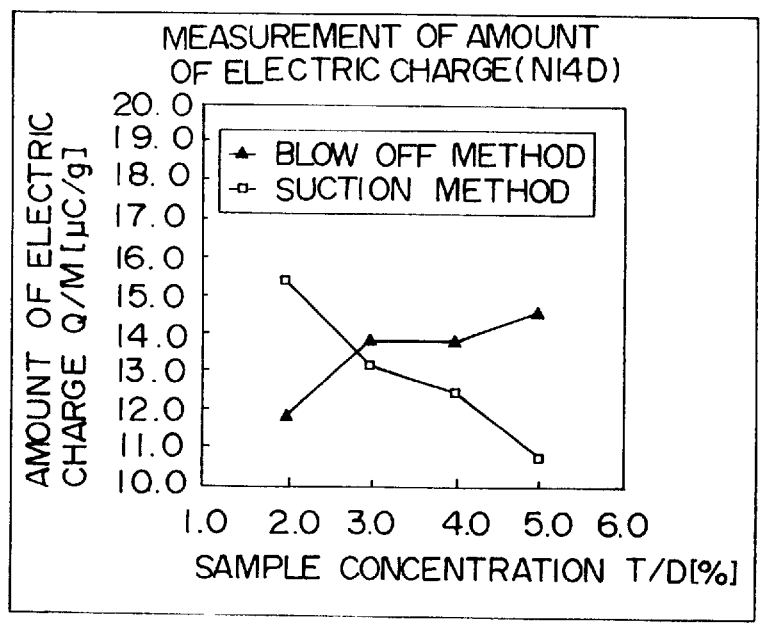
Figure 4:
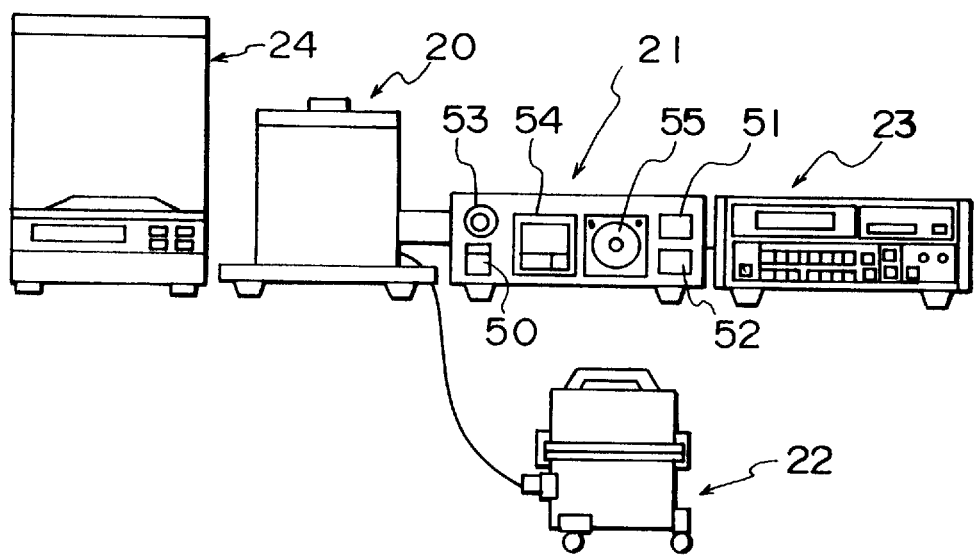
Figure 5:
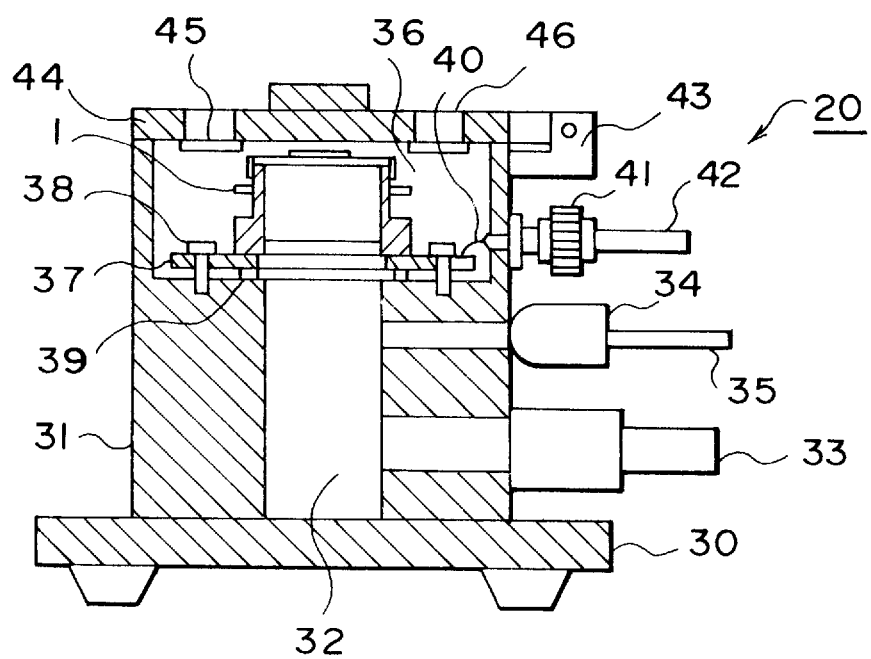

as measured relying upon a conventional carbon analyzer method (▲) and the suction method of the present invention (□);

FIG. 3 is a graph showing the amount of charge of a two-component developing agent (T/D has been known) as measured relying upon a conventional blow-off method (▲) and the suction method of the present invention (□);

FIG. 4 is a diagram illustrating the arrangement of the whole measuring apparatus used in the present invention; and FIG. 5 is a sectional view illustrating the measuring apparatus in detail.

DETAILED DESCRIPTION OF THE INVENTION

Figure 1:
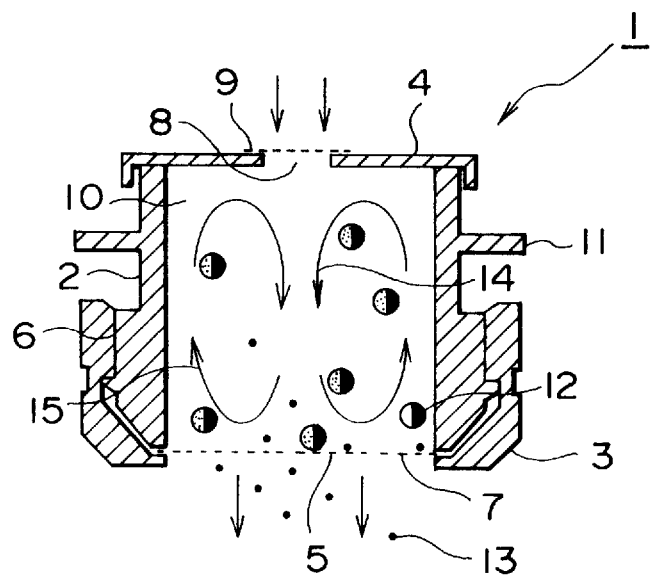
FIG. 1 is a diagram illustrating a principle of measurement according to the present invention.

Referring to FIG. 1 for explaining the principle of measurement according to the present invention, a unit cell 1 comprises a cylindrical member 2, a lower cover 3 and an upper cover 4. The lower cover 3 has an opening 5 having a diameter same as the inner diameter of the cylindrical member 2. The lower cover 3 and the cylindrical member 2 are fastened together by a screw 6, and a mesh 7 is held between them.

A ventilation hole 8 of a diameter smaller than the inner diameter of the cylindrical member 2 is formed at the center of the upper cover 4, and is provided with a mesh 9 for preventing the powder from scattering. The upper cover 4 is placed on the upper part of the cylindrical member 2 so as to be opened and closed, enabling the developing agent to be introduced into, or taken out from, a developing agent container 10. A grip portion (ring) 11 is formed along the outer circumference of the cylindrical member 2.

The mesh 7 of the unit cell 1 has a mesh opening which does not permit the passage of a carrier 12 in the developing agent but permits the passage of a toner 13 in the developing agent. The unit cell 1 is made of an electrically conducting material and, particularly, a metal so that the amount of electric charge can be measured. The mesh 7 is made of the same material, too.

After the developing agent space 10 in the unit cell 1 is filled with the developing agent, the upper cover 4 is fitted thereto and the air is sucked from the lower side of the mesh 7. The ventilation hole 8 is formed at the central portion of the upper cover 4, the ventilation hole 8 having an area smaller than the area of the mesh 7. Due to the air stream flowing into the developing agent space, therefore, there occurs a circulatory stream consisting of a downward stream 14 of the developing agent at the center and an upward stream 15 thereof along the wall of the cylindrical member 2. There also occurs a turbulent stream on the outer side of an imaginary truncated cone that connects the edge of the ventilation hole 8 to the edge of the mesh 7.

Due to the circulatory stream or, further, due to the turbulent stream, the carrier 12 and the toner 13 in the developing agent are separated from each other, the toner 13 that is separated is discharged out of the unit cell 1 through the mesh 7 being carried by the air stream. This operation is continued for a predetermined period of time, so that the carrier 12 and the toner 13 are effectively separated from each other.

As the toner is separated and discharged, the electric charge of the carrier 12 generates (remains) in the unit cell 1. Since this residual electric charge has an absolute value which is equal to the electric charge of the toner, the amount of electric charge [$\mu c/g$] of the toner is measured in compliance with the following formula (1), Amount of electric charge Q/M=−Amount of electric charge [$\mu c$] generated during the suction/Weight of toner [g] sucked (1)

At this moment, furthermore, when the difference in the weight is measured, the toner concentration [%] is measured in compliance with the following formula (2), Toner concentration T/D=Weight of toner [g] sucked/Weight of developing agent introduced [g] (2)

The weight of the toner [g] that is sucked is expressed by the following formula (3), Weight of toner [g] sucked=Weight of developing agent [g] introduced—Weight of residual developing agent [g] (3)

According to the present invention, the carrier and the toner in the developing agent are separated from each other by utilizing the circulatory stream or turbulent stream of the developing agent created by sucking the air in the unit cell. To effectively accomplish the separation, the area [$S1=\pi(D1)^2/4$] of the ventilation hole 8 must be from 1.6 to 25%, particularly, from 6.3 to 14.1% and, most desirably, from 6.3 to 9.0% of the area [$S2=\pi(D2)^2/4$] of the mesh 7, and the distance (height H) from the ventilation hole 8 to the mesh 7 and the diameter (D2) of the mesh 7 must satisfy a relation $0.5 \leq (H/D2) \leq 1.25$.

That is, when the area ratio of the ventilation hole 8 is smaller than the above-mentioned range, the amount of the air flowing into the unit cell is so small that the circulatory stream is not created and the toner is not separated to a sufficient degree. When the area ratio of the ventilation hole 8 is larger than the above-mentioned range, on the other hand, the developing agent is attracted by the mesh 7, and the circulatory stream loses stability and the toner is not separated to a sufficient degree.

When H/D2 becomes larger than 1.25, furthermore, the air stream in the unit cell becomes a laminar flow, whereby the circulatory stream is not formed to a sufficient degree and the toner is not effectively separated. When H/D2 becomes smaller than 0.5, on the other hand, the upward stream becomes insufficient in the unit cell, the circulatory flow is not formed to a sufficient degree and the toner is not effectively separated, either.

According to the present invention as described above, it is made possible to simultaneously measure the toner concentration T/D and the amount of electric charge Q/M through a single operation using a common measuring apparatus, presenting advantage in that both the concentration and the amount of electric charge can be measured from a developing agent of which the toner concentration and composition have not been known.

According to the present invention, furthermore, the toner concentration and the amount of electric charge can be measured by a simple means maintaining precision.

Figure 2:
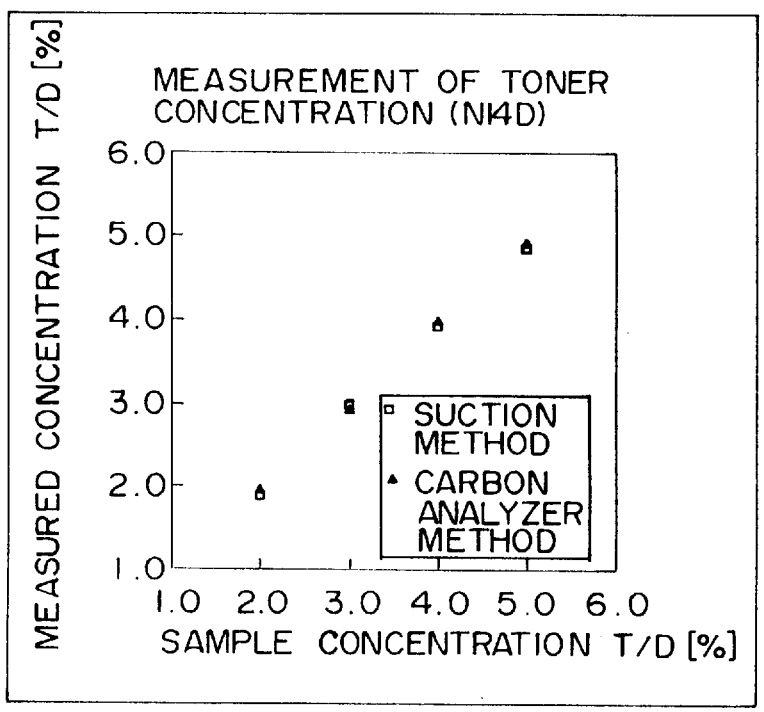
FIG. 2 is a graph showing the toner concentration (T/D) of a two-component developing agent (T/D has been known)

FIG. 2 illustrates the measurement of the toner concentration (T/D) of a two-component developing agent (T/D has been known) relying upon a conventional carbon analyzer method (▲) and a suction method of the present invention (□)(details will be described in an embodiment appearing later). It will be understood from FIG. 2 that the toner concentration is obtained just like the sample concentration featuring a high precision. It will be further understood that the present invention is superior in regard to simplicity of the apparatus and easily operation.

FIG. 3 illustrates the measurement of the amount of electric charge of a two-component developing agent (T/D has been known) relying upon a conventional blow-off method (▲) and the suction method of the present invention (□) (details will be described in the embodiment appearing later). From FIG. 3, the amount of electric charge changes quite differently for the toner concentration between the blow-off method and the method of the present invention. It is, however, considered that the method of the present invention is indicating a proper tendency from the fact that the amount of electric charge of the toner increases with a decrease in the toner concentration.

The blow-off method and the method of the present invention are in common in regard to utilizing the air stream for separating the toner. According to the blow-off method, however, the gas pressure is so high that the carrier is destroyed. As the carrier is destroyed, it is considered that an excess of positive or negative electric charge is generated depending upon the type of the carrier.

According to the present invention which is based upon the suction, on the other hand, the gas pressure is not larger than one atmosphere even at the highest, which is not quite comparable with the pressure of the blow-off method. Even though the gas pressure is low, the toner is completely separated owing to the creation of a circulatory stream or a turbulent stream. It has been observed by an electron microscope that the carrier is not destroyed.

In the apparatus of the present invention, a hollow unit cell support plate is provided at an upper part of the suction chamber maintaining air-tightness and electric insulation, and the unit cell is detachably supported on the support plate.

This constitution not only makes it possible to introduce or take out the developing agent into or out of the unit cell but also makes it possible to measure the weight inclusive of the unit cell. By simply placing the unit cell on the support plate, therefore, it is allowed to carry out the suction operation and to measure the electric charge.

With the unit cell and the support plate being made of metal materials having a difference in the work function of not larger than 0.60 eV and, particularly, being made of the same metal material, it is possible to precisely measure the amount of electric charge.

EMBODIMENT

Referring to FIG. 4 illustrating the arrangement of the whole measuring apparatus used in the present invention, the apparatus comprises a main measuring apparatus 20, a main apparatus control unit 21, a suction pump 22, a voltameter 23 and a balance 24.

Referring to FIG. 5 illustrating the structure of the main measuring apparatus 20 in detail, a plate 30 made of, for example, a stainless steel (SUS) is provided under the main apparatus 20, and a shielding case 31 made of the stainless steel is provided on the plate 30.

A suction chamber 32 having an opening in the upper portion thereof is provided in the shielding case 31, and is connected to the suction pump 22 through a hose 33. An atmospheric pressure sensor 34 is disposed in the suction chamber 32, and its detection signal is fed to the main apparatus control unit 21 through a cable 35.

A unit cell chamber 36 is provided in the upper part of the suction chamber 32, and a unit cell support plate 37 which also works as an electrode is provided at a boundary between the unit cell chamber 36 and the suction chamber 32. The support plate 37 is also made of a stainless steel and is fastened to the shielding case 31 using stud bolts 38 made of an electrically insulating material (resin). A ring-like electrically insulating material (silicone rubber) 39 is fitted between the support plate 37 and the shielding case 31, and the support plate 37 is provided in the main apparatus 20 maintaining air-tightness and electric insulation. The support plate 37 is connected to the voltameter 23 through an internal wiring 40, a connector 41 and a cable 42.

A cover 44 is attached to the upper part of the unit cell chamber 36 via hinges 43 so as to be opened and closed. The cover 44 has a ventilation port 46 which is equipped with a filter 45 (400 mesh).

Reverting to FIG. 4, the operation panel of the main apparatus control unit 21 is provided with a power source switch 50, a start button 51, a stop button 52, a suction force-adjusting knob 53, a digital barometer 54 and a timer 55.

The start button 51 and the stop button 52 work to drive the suction pump 22 to start taking measurement and work to stop the suction pump 22 to discontinue the measurement. The timer 55 works to stop the pump 22 when a measuring time that is set has elapsed.

The suction force-adjusting knob 53 is used to control the electric power supplied to the suction pump 22 relying upon a triac. The digital barometer 54 displays the atmospheric pressure detected by the atmospheric pressure sensor 34 (FIG. 5). Upon turning the suction force-adjusting knob 53, it is allowed to set the pressure in the suction chamber 32 (FIG. 5) to any value.

The suction pump 22 works to decrease the pressure in the suction chamber 32 (FIG. 5) down to a predetermined pressure and to trap the toner particles that are discharged. Preferably, the suction pump 22 accomplishes a vacuum degree of from 300 to 1200 mm-water column and a blow rate of from 0.01 to 1.00 m$^3$/min, and is equipped with a paper pack for trapping the toner. The pump used in this embodiment is a toner cleaner or, more concretely, a cleaner, Model CV-TN95, manufactured by Hitachi, Ltd.

The voltameter 23 is to measure the electric charge of the residual carriers, i.e., to measure the electric charge of the toner via the support plate electrode 37, and has a measuring range of a maximum of 20 $\mu$C. The voltameter used in this embodiment is a digital electrometer, Model TR8652, and a coulomb range extender, Model R12601 (which is used only when the measuring range needs be extended) manufactured by Advantest Co.

The balance 24 is to measure the weight of the developing agent or of the residual carrier inclusive of the unit cell, and features a precision of not lower than the fourth decimal point, since the amount of the toner that is sucked is as small as from about 0.01 to about 0.05 g. In this embodiment, use is made of an electronic even balance, Model AEG-320, manufactured by Shimazu Mfg. Co., having a reading limit of 0.1 mg.

The conditions for measuring the toner concentration and the amount of electric charge thereof differ to a considerable degree depending upon the kind of the carrier, kind of the toner and their combination, and cannot be exclusively determined. Generally, however, the measuring conditions should be such that the suction pressure is from −6 kPa to −13 kPa, the suction time is from 20 to 60 seconds, and the amount of the developing agent sample is from 0.4 to 1.0 g. Preferably, furthermore, the mesh has an area of from 3 to 20 cm$^2$ and the developing agent space has a volume of from 6 to 70 cm$^3$. It is further desired that the mesh has an opening degree of 400 mesh (Tyler standard).

When the degree of pressure reduction is too small or the time for reducing the pressure is too short, the toner and the carrier are not completely separated from each other, and the toner concentration T/D tends to become small or the amount of electric charge Q/M tends to be varied. When the degree of pressure reduction is too high or the time for reducing the pressure is too long, the carrier is partly destroyed, whereby the toner concentration T/D tends to become large and the amount of electric charge Q/M undergoes a change due to excess of electric charge generated in the cell.

It needs not be pointed out that the degree of reducing the pressure and the time for reducing the pressure should be changed to set an optimum range, since the developing agent contains the carrier that is destroyed easily or the toner that cannot be easily separated.

When the amount of the developing agent sample is larger than the above-mentioned range, the toner scatters in an increased amount in the apparatus. When the amount of the developing agent sample is smaller than the above-mentioned range, on the other hand, the amount of the toner becomes so small that the precision decreases.

According to this embodiment, the measurement was taken in accordance with the following procedure.

1. Measure the weight of the unit cell. . . . A [g]
2. Put the sample into the unit cell.
3. Measure the weight of the unit cell containing the sample. . . . B [g]
4. Set the unit cell to the apparatus.
5. Reset the voltameter to zero.
6. Depress the start button to start the suction.
7. Hold the voltameter in case the power goes off, and read the value at that moment. . . . C [μC]
8. Measure the weight of the unit cell. . . . D [g]
9. Clean the unit cell.
10. Calculation.

$$\text{Amount of electric charge } Q/M \ [\mu C/g] = \frac{C[\mu C]}{B - D[g]} \quad (4)$$

$$\text{Toner concentration } T/D = \frac{B - D[g]}{B - A[g]} \times 100 \ [\%] \quad (5)$$

As the unit cell, use was made of a stainless steel cell (with a 400-mesh stainless steel gauze) having a mesh diameter ($D_2$) of 40 mm, the upper opening diameter ($D_1$) of 12 mm, a height (H) of X (see Table 1) mm and a weight of 155 g. Table 1 shows the experimental results of when the carrier and the toner were separated from each other by suction while changing the height (H) (X-value).

TABLE 1

| H (mm) | 18 | 20 | 30 | 40 | 50 | 52 |
|---|---|---|---|---|---|---|
| H/$D_2$ | 0.45 | 0.50 | 0.75 | 1.00 | 1.25 | 1.30 |
| Results | X | ○ | ○ | ○ | ○ | X |

In Table 1, ○ represents that the toner and the carrier were completely separated from each other, and X represents that the toner which was not separated stayed in the carrier.

The measurement was taken under the standard conditions of a suction pressure of −9 kPa, a suction time of 30 seconds, and a sampling amount of from 0.4 to 1 g.

As an example, use was made of a developing agent for an electrophotographic copying machine, Model DC-2556, manufactured by Mita Kogyo Co. By using the above-mentioned unit cell of X=30 mm, the toner and the magnetic carrier were correctly measured and were treated in a ball mill to prepare a two-component developing agent having a toner concentration of from 2 to 5%. The toner concentration and the amount of electric charge were measured under the above-mentioned conditions.

For the purpose of comparison, the toner concentration was measured according to the known carbon analyzer method and the amount of electric charge of the toner was measured according to the known blow-off method.

The results were as shown in FIGS. 2 and 3.

The present invention gives an advantage in that the toner concentration and the amount of electric charge can be simultaneously measured with short periods of time through a single suction operation by using a common measuring apparatus.

Moreover, the toner concentration and the amount of electric charge can be measured using a simply constructed apparatus maintaining precision, offering such advantages that the apparatus is obtained at a reduced cost and the running cost can be decreased, as well.

Besides, since no conversion formula is required, it is allowed to measure the toner concentration of a developing agent of which the concentration and the composition have not been known. The toner concentration is not affected by the spent toner, either.

Moreover, the circulatory stream and turbulent stream created by the suction enable the toner to be effectively separated without destroying the carrier. It is therefore possible to correctly measure the amount of electric charge of the toner.

What is claimed is:

1. An apparatus for measuring the toner concentration and the amount of electric charge of a two-component developing agent, comprising:

a unit cell for measurement having a two-component developing agent space therein, a mesh in the lower portion thereof and a single ventilation hole in the upper central portion thereof;

a suction chamber; and a hollow unit cell support plate which is provided at an upper part of the suction chamber maintaining air-tightness and electric insulation and is also serving as an electrode;

wherein the ventilation hole in said unit cell has an area which is from 1.6 to 25% of the mesh area, and the developing agent space in the unit cell has a height which is from 0.5 to 1.25 times as great as the diameter of the mesh.

2. An apparatus according to claim 1, wherein the unit cell and the support plate are made of metal materials having a difference in work function which is not larger than 0.60 eV.

3. A method of measuring the toner concentration and the amount of electric charge of a two-component developing agent consisting essentially of a toner and a magnetic carrier, by filling a unit cell having a mesh in the lower portion thereof and a small ventilation hole at the upper central portion thereof with the two-component developing agent, wherein the area of the ventilation hole is from 1.6 to 25% of the area of the mesh, and the distance between the ventilation hole and the mesh is from 0.5 to 1.25 times as great as the diameter of the mesh, creating a suction in the lower portion of the unit cell and creating a downward stream of the developing agent at the central portion of the unit cell and an upward stream of the developing agent along the walls of the unit cell relying upon the suction through said mesh to separate the toner from the magnetic carrier, discharging the separated toner out of the unit cell through the mesh, calculating the toner concentration from the reduction in the weight of the developing agent in the unit cell or from the amount of the discharged toner and calculating the amount of electric charge of the toner from the amount of electric charge of the unit cell.

4. A method according to claim 1 wherein the suction pressure is −6 kPa to −13 kPa and the suction time is 20 to 60 seconds.

5. An apparatus for measuring the toner concentration and the amount of electric charge of a two-component developing agent, comprising:

- a unit cell for measurement having a two-component developing agent space therein, a mesh in the lower portion thereof and a single ventilation hole in the upper central portion thereof;
- a suction chamber; and
- a hollow unit cell support plate which is provided at an upper part of the suction chamber maintaining airtightness and electric insulation and is also serving as an electrode;
- wherein the ventilation hole in said unit cell has an area which is from 6.3 to 14.1% of the mesh area, and the developing agent space in the unit cell has a height which is from 0.5 to 1.25 times as great as the diameter of the mesh.

6. An apparatus according to claim 5, wherein the unit cell and the support plate are made of metal materials having a difference in work function which is not larger than 0.60 eV.

7. A method of measuring the toner concentration and the amount of electric charge of a two-component developing agent consisting essentially of a toner and a magnetic carrier, by filling a unit cell having a mesh in the lower portion thereof and a small ventilation hole at the upper central portion thereof with the two-component developing agent, wherein the area of the ventilation hole is from 6.3 to 14.1% of the area of the mesh, and the distance between the ventilation hole and the mesh is from 0.5 to 1.25 times as great as the diameter of the mesh, creating a suction in the lower portion of the unit cell and creating a downward stream of the developing agent at the central portion of the unit cell and an upward stream of the developing agent along the walls of the unit cell relying upon the suction through said mesh to separate the toner from the magnetic carrier, discharging the separated toner out of the unit cell through the mesh, calculating the toner concentration from the reduction in the weight of the developing agent in the unit cell or from the amount of the discharged toner and calculating the amount of electric charge of the toner from the amount of electric charge of the unit cell.

8. A method according to claim 7, wherein the suction pressure is −6 kPa to −13 kPa and the suction time is 20 to 60 seconds.

* * * * *